United States Patent
Sauvaigo

(10) Patent No.: US 9,617,580 B2
(45) Date of Patent: Apr. 11, 2017

(54) METHOD FOR THE QUANTITATIVE ASSESSMENT OF GLOBAL AND SPECIFIC DNA REPAIR CAPACITIES OF AT LEAST ONE BIOLOGICAL MEDIUM, AND THE APPLICATIONS THEREFOR

(71) Applicant: Sylvie Sauvaigo, Herbeys (FR)

(72) Inventor: Sylvie Sauvaigo, Herbeys (FR)

(73) Assignee: Commissariat À L'Energie Atomique Et Aux Energies Alternatives, Paris (FR)

( * ) Notice: Subject to any disclaimer, the term of this patent is extended or adjusted under 35 U.S.C. 154(b) by 0 days.

(21) Appl. No.: 14/336,453

(22) Filed: Jul. 21, 2014

(65) Prior Publication Data

US 2015/0031580 A1    Jan. 29, 2015

Related U.S. Application Data

(63) Continuation of application No. 10/539,769, filed as application No. PCT/FR03/03816 on Dec. 19, 2003, now abandoned.

(30) Foreign Application Priority Data

Dec. 20, 2002 (FR) ...................................... 02 16435

(51) Int. Cl.
*C12Q 1/68* (2006.01)

(52) U.S. Cl.
CPC ...................................... *C12Q 1/68* (2013.01)

(58) Field of Classification Search
None
See application file for complete search history.

(56) References Cited

U.S. PATENT DOCUMENTS

| | | |
|---|---|---|
| 6,309,838 B1 | 10/2001 | Chaubron et al. |
| 7,033,757 B2 | 4/2006 | Makrigiorgos |
| 2002/0022228 A1 | 2/2002 | Nehls et al. |

FOREIGN PATENT DOCUMENTS

WO    WO 99/49080    3/1999

OTHER PUBLICATIONS

Calsou et al., "Double Strand Breaks in DNA Inhibit Nucleotide Excision Repair In Vitro" 271(44) The Journal of Biological Chemistry 27601-27607 (1996).*
Wood, et al., "Complementation of the Xeroderma Pigmentosum DNA Repair Defect in Cell-Free Extracts", Cell, vol. 53,pp. 97-106, Apr. 8, 1988.
You, et al., "Bulge Defects Do Not Destabilize Negatively Supercoiled DNA", Biophysical Journal: Biophysical Letters, L 43-45 (2005).
Meselson, et al., Equilibrium Sedimentation of Macromolecules in Density Gradients. PNAS 43(7):581-8 (1957).
Chiu, et al., Synergistic Effects of Epoxy-and amine-silanes on Microarray DNA Immobilization and Hybridization Biochem. 374(3):625-32 (2003).
Zierdt, et al., Adherence of bacteria, yeast, blood cells and latex spheres to large-porosity membrance filters. Appl. Environ. Microbiol. 38(6):1166-72 (1979).
Yershov, et al., DNA analysis and diagnostics on oligonucleotide microchips PNAS 93(10):4913-8 (1996).
Kreklau, et al., "A Novel Fluorometric Oligonucleotide assay . . . DNA glycolase", J. Nucleic Acids Res. 2001, vol. 29, No. 12, pp. 2558-2566.
Randerath, et al., "32P-labeling test for DNA storage", PNAS 78 (10):6126-9 (1981).
Douki, et al., "Inter-strand phtoproducts are produced in high yield within DNA exposed to UVC radiation", Nuc. Acid Res. 32(12):3134-3142 (2003).
Gelfand, et al., "A quantitative method for evaluating the stabilities of nucleic acids", PNAS 96:6113-6118 (1999).

* cited by examiner

*Primary Examiner* — Nancy J Leith
(74) *Attorney, Agent, or Firm* — William E. Beaumont

(57) ABSTRACT

A method for quantitative assessment of base excision repair (BER) and nucleotide excision repair (NER) DNA capacities of one or more cellular extracts using supercoiled plasmid DNA by characterizing lesions on the plasmids relative to a control.

30 Claims, 3 Drawing Sheets

1  Plasmid + DDE

2  Control plasmid

3  Plasmid + endoperoxide (endo)

4  Plasmid  + UVC 0.12 J/cm$^2$ (UVC1)

5  Plasmid  + UVC 0.06 J/cm$^2$ (UVC2)

6  Plasmid  + UVC 0.03 J/cm$^2$ (UVC3)

METHOD FOR THE QUANTITATIVE ASSESSMENT OF GLOBAL AND SPECIFIC DNA REPAIR CAPACITIES OF AT LEAST ONE BIOLOGICAL MEDIUM, AND THE APPLICATIONS THEREFOR

TECHNICAL FIELD

The present invention relates to a method for the quantitative assessment of the overall and specific DNA repair capacities of a biological medium, by assessing the excision/resynthesis capacities of said medium, and also to the applications thereof.

BACKGROUND OF THE INVENTION

DNA is continuously subjected to endogenous or exogenous attacks that result in the formation of base or sugar lesions.

The lesions include:
- lesions of purine or pyrimidine bases: oxidative lesions induced by the cellular metabolism and by photosensitization; lesions through the formation of chemical adducts, which result from the harmful action of many genotoxic agents, such as polycyclic hydrocarbons, contained in combustion products; lesions through the formation of metheno-bases or of etheno-bases;
- lesions of the structure of the DNA double helix: formation of intrastrand (between two adjacent bases of the same strand) or interstrand (between two bases located on the homologous strands) bridges, generally caused by ultraviolet radiation (formation of bridges between pyrimidines, which become dimeric) or bifunctional antitumor agents, such as cisplatin and intercalating agents, which form stable covalent bonds between the bases carried by opposite strands;
- spontaneous lesions, due to the fact that DNA is a partially unstable molecule: spontaneous deaminations or depurinations;
- lesions through single-stranded or double-stranded breakage: produced by agents such as ionizing radiation and through the action of free radicals;
- sugar lesions: the destruction of a deoxyribose results in breakage of phosphodiester bonds in the damaged site, followed by strand breakage.

The diversity of the induced lesions is illustrated by analyzing the stable photoproducts detected following UVC irradiation: alongside the pyrimidine dimers due to the formation of a cyclobutane ring, pyrimidine (6-4) pyrimidones form between two adjacent pyrimidines. The relative proportion of the pyrimidine dimers and (6-4) products ranges from 10 to 4 for 1. Their respective effectiveness in the lethal effect and in the mutagenic effect of ultraviolet radiation is also different: the dimers have a greater cytotoxic role than the (6-4) products, whereas the reverse is true for the mutagenic effect. Similarly, ionizing radiation (γ-rays from cobalt 60, for example) simultaneously produces single-stranded or double-stranded breakages (approximately in the ratio of 9 to 1), many base addition products, base losses and, at high doses, bridges between DNA and adjacent proteins (chromosomal, for example). On average, one strand breakage is counted per modified base. The predominant role of double-stranded breakage in the cytotoxic effect of radiation is accompanied by a mutagenic effect due to base alterations.

These various types of lesions can be created on isolated DNA. For example, (6-4) photoproduct-type lesions and cyclobutane-type pyrimidine dimers are induced by UVC irradiation (Hoeijmaker et al., *Mutation Res.*, 1990, 236, 223-238); oxidative-type lesions are induced by Fenton's reaction in the presence of hydrogen peroxide and iron (Elliot et al., *Free Rad. Biol. Med.*, 2000, 1438-1446). Another means of preparing modified DNA consists in manipulating plasmids by means of molecular biology techniques and inserting therein an oligonucleotide obtained by chemical synthesis and containing a lesion of interest (Biade et al., *J. Biol. Chem.*, 1997, 273, 898-902).

All living organisms have DNA repair systems intended to maintain the integrity of their genome.

Among these repair systems, two have the function of eliminating modified bases from the DNA: they are the base excision repair (BER) system and the nucleotide excision repair (NER) system:
- the BER system is more specifically dedicated to the repair of small lesions in DNA, such as oxidative damage, abasic sites, base fragmentations, base methylations, etheno-bases, etc.
- the NER system takes care of bulky lesions that induce distortion of the DNA double helix, such as acetylaminofluorine-DNA, cisplatin-DNA and psoralen-DNA adducts, dimers derived from UVB and UVC irradiation of DNA, covalent lesions formed between a DNA base and another molecule, etc. (Sancar et al., *Annu. Rev. Genetics*, 1995, 29, 69-105).

These various repair systems have common characteristics, and in particular the following steps:
- recognition of the lesion(s) by proteins belonging to the repair system,
- excision of the lesion and, optionally, of the adjacent nucleotides,
- resynthesis of the missing nucleotides by polymerases in the medium,
- the repair generally ends with ligation of the neoformed strand with the existing DNA strand.

In all these cases, this process comprises the elimination of the modified nucleotide and the incorporation, as a replacement in the DNA chain, of at least one nucleotide triphosphate present in the repair medium.

It should, however, be noted that repair systems, especially in eukaryotes, are very complex and many variants of this simplistic configuration exist (overall repair, repair associated with the DNA transcription, repair associated with DNA replication, etc.). Some proteins are involved in several repair systems simultaneously, others are specific for a single system, some can be induced by cellular or external factors, others have a ubiquitous and constant expression.

For the remainder of the description:

The term "substrate" refers to any DNA that may undergo a repair reaction in the presence of cell extracts and, by extension, the DNA lesions.

The term "biological medium" or "cell extract" refers to a purified by unpurified biological preparation that may contain at least one enzyme activity related to DNA repair.

A lesion can generally be associated with the specific proteins responsible for its repair in the DNA. Differences exist according to species: in prokaryotes such as *Escherichia coli*, the enzymes are less specific, whereas in humans, a much stricter lesion-specific repair enzyme association is observed, especially in the BER system. For example, Lindahl and Wood (Science, 1999, 286, 1897-1905) describe the BER system enzymes that are the most important in humans and also the lesions that are associated therewith. For example, in humans, the OGG1 protein, which is a glycosylase belonging to the BER system, is associated with the repair of 8-oxo-2'-deoxyguanosine. In *Escherichia coli*, formamidopyrimidine-DNA N-glycosylase repairs this same lesion, but more generally also oxidized purine bases (Seeberg et al., TIBS, 1995, 20, 391-397). The human protein ANPG is the equivalent of the bacterial protein AlkA. These enzymes do not, however, have the same affinities for their substrates and have different excision rate constants (Laval et al., Mut. Res., 1998, 402, 93-102). More than about forty different lesions that are taken care of by the BER system can have considerable and negative biological consequences if they are not repaired. It is considered that the enzymes responsible for their repair have a considerable antitumor role. It can be seen that precise knowledge of their substrate specificities is very important.

Cellular repair capacity assays have been developed and can be classified in two categories: in vitro assays that require the use of active cell extracts, and in vivo or semi in vivo systems carried out on live cells.

I. Methods Based on Measuring Excision/Resynthesis Activity

A. Most of the in vitro assays have been developed on the basis of the experiments described by Wood et al. (*Cell*, 1988, 53, 97-106 and *Biochemistry*, 1989, 26, 8287-8292), which assess the excision/resynthesis step of the repair.

More precisely, this assay comprises the use of a plasmid DNA into which lesions are introduced (by UV irradiation: formation of pyrimidine dimers, bridges; through the action of DNase I: single-stranded cleavage or breakage); the DNA thus modified is incubated at 30° C. in the presence of a repair preparation comprising at least: the cell extract to be assessed, a nucleotide triphosphate labeled in the alpha-position with $^{32}P$ and ATP. The enzymes contained in the extract incise the plasmid DNA and eliminate the lesions. DNA is synthesized de novo by replacement of the eliminated nucleotides. The radioactive nucleotide introduced into the medium is incorporated into the DNA during the synthesis. After isolation of the repaired plasmid by agarose gel electrophoresis, the amount of radioactivity incorporated, which is proportional to the rate of repair of the substrate, is measured. The method of preparing the cell extract and the reaction conditions influence the quality of the repair. In particular, it appears that the best repair yield is obtained with whole cell extracts of the type of those used for in vitro transcriptions, whereas cytosolic extracts of the type of those used for promoting plasmid replication from an SV40 origin, and also other crude cell extracts, exhibit nuclease activity, which does not allow correct interpretation of the repair.

Under the conditions established by Wood et al., the specificity of the reaction as regards the irradiated DNA is greater in the presence of a KCl concentration of the order of 40-100 mM. In addition, the irradiated DNA replication, which takes place during repair, is highly dependent on the presence of ATP and of an ATP-regenerating system (phosphocreatine+creatine phosphokinase), with a view to maintaining a constant level of ATP, the maintaining of this level being more specifically associated with the incision step of the repair. Such a dependency is not, for example, encountered in cases of strand breakage repair. A control sample, consisting of the same plasmid that has not been modified, is used simultaneously in the reaction mixtures.

The assay from Wood et al. requires the use of radioactive labels, which imposes restrictions that limit the implementation of this method in routine assays; in addition, this assay does not have sufficient qualities of simplicity and of practicality for it to be used routinely.

The method of Wood et al. has been proposed in assays characterizing extracts originating from cells established from patients suffering from *xeroderma pigmentosum* (Satoh et al., Proc. Natl. Acad. Sci. USA, 1993, 90, 6335-6339; Jones et al., Nucl. Acids Res., 1992, 20, 991-995; Robins et al., EMBO J., 1991, 10, 3913-3921). Xeroderma pigmentosum is a multigenic, multiallelic, autosomal recessive disease. Cells originating from patients suffering from this disease are very sensitive to ultraviolet radiation and exhibit DNA repair deficiencies. Eight genes are involved in the various complementation groups of this disease: XPA to XPG and the variant group XPV. Each group has different characteristics relating to DNA repair and in particular to the various NER subtypes. DNA lesions, whether they belong to the small lesion category or the bulky lesion category, are repaired differently, according to the complementation group.

Other repair diseases (Cockayne Syndrome, *Ataxia Telangectasia*) also have specific repair characteristics and have been studied by the method of Wood et al.

B. In various publications, the team of B. Salles and P. Calsou (Biochimie 1995, 77, 796-802; Anal. Biochem. 1995, 232, 37-42) describes a method for detecting DNA lesions by carrying out excision/resynthesis reactions on a plasmid attached in wells of microplates. The plasmid is adsorbed in microplate wells and then modified, a posteriori, with chemical agents. Cell extracts are added to the wells along with digoxigenin-labeled nucleotide triphosphates. The label is incorporated into the DNA, if lesion excision has occurred, during the resynthesis step. The label is then revealed in each well by means of an antibody coupled to alkaline phosphatase. A substrate that becomes luminescent after dephosphorylation by alkaline phosphatase is added to each well. The luminescent signal, emitted in each well, is measured. It is proportional to the rate of incorporation of the label.

This method is also described in international application WO 96/28571, the inventors of which also belong to the team of B. Salles and P. Calsou, and which describes a method for qualitatively and quantitatively detecting DNA lesions, in which DNA with lesions is attached to a solid support and a composition comprising a cell extract to be tested and containing labels is brought into contact with said DNA with lesions (prior or subsequent to the attachment to said solid support). They consider that their method makes it possible to simultaneously process a large number of samples; if reference is made to the examples, the repair in the presence of a cell extract is carried out in a reaction medium of 50 μl, using an extract comprising 150 μg of proteins, 50 mM of KC, 5 mM of magnesium chloride, DTT, phosphocreatine, phosphocreatine kinase and various dNTPs, one of them being labeled with digoxigenin. The repair is obtained after incubation for 3 hours at 30° C. and the wells are washed with a washing solution comprising a phosphate buffer with a salt, to which a nonionic surfactant (Tween 20) is added in a proportion of 0.05 and 0.15% (preferred composition: 10 mM phosphate buffer, 137 mM NaCl and 0.1% Tween 20). It is specified that this assay is highly sensitive, insofar as the detection is carried out on 40 ng of DNA instead of 200 or 300 ng, in the case of an assay solution.

The assay by the team of B. Salles and P. Calsou essentially proposes modifying the plasmid after attachment to the solid support. Now, it is known that, included among the lesions created by many chemical or physical agents are chain breakages. Now, these breakages are repaired very rapidly and effectively by active cell extracts. With this assay, it is therefore impossible to differentiate between breakage repair and the repair of other lesions. Breakage repair can even mask the repair of other lesions and interfere with the signals attributed to the repair of other DNA lesions. It is therefore a system that allows the detection of an overall effect, without identifying the lesions recognized by the repair systems; in addition, the aim of this method is not to detect and quantify the activity of the proteins involved in the DNA repair, but to identify the presence of lesions on the DNA processed.

II. Methods Based on Assessing the Incision/Excision Step

Variants of the method by Wood et al. have been proposed and make it possible in particular to measure only the lesion incision activity:

A. Redaelli et al. (Terat. Carcinog. Mut., 1998, 18, 17-26) describe a method in which the plasmid is incubated directly with the extract without the nucleotide triphosphates. Cleavages in the supercoiled plasmid bring about a change in migration rate in the agarose gel during electrophoresis. The supercoiled plasmid migrates faster that the incised plasmid, due to its conformation. The bands corresponding to the various forms of the plasmid are quantified; the amount of the incised form is correlated with the activity of incision of the lesions of the plasmid, containing the extract.

More precisely, this article studies the incision action of AP-endonuclease, that occurs on an a basic site, obtained after the action of a glycosylase specific for the modification to be repaired (alkylation, hydrolytic deamination, oxidation, mismatching), by cleaving the deoxyribose phosphodiester linkage positioned 3' or 5' of this abasic site. In this article, the AP-endonuclease activity is more specifically studied on a crude extract of human lymphocytes. The extract (80 µl) is incubated, firstly, with an undamaged plasmid (control) and, secondly, with a depurinated plasmid. It is thus found to be possible to quantify the activity of AP-endonuclease insofar as the incision activity is dependent on the damage and sensitive to EDTA.

B. The team of P. Calsou and B. Salles (Biochem. Biophys. Res. Corm., 1994, 202, 788-795) proposes another approach for specifically measuring the activity of incision of the lesions of a plasmid. They introduce into the repair medium an inhibitor specific for eukaryotic polymerases, aphidicolin, in order to prevent resynthesis, by the endogenous polymerases, of the normal DNA fragments after the first excision step. An exogenous prokaryotic polymerase is mixed with the reaction medium in an equivalent amount for all the tubes. Differences in the results obtained thus reflect the lesion excision step and not the resynthesis of the excised DNA fragments.

C. Another method based on a modification of the comet assay (gel electrophoresis, in an alkali medium, of a single cell) also makes it possible to measure incision activity. It was developed by Collins et al. (Mutagenesis, 2001, 16, 297-301). Oxidative lesions are introduced into the genomic DNA by photosensitization of HeLa cells in the presence of visible light. The cells are then incorporated into an agarose gel spread onto a microscope slide, and the cell membranes and the proteins are then eliminated by controlled lysis. The nucleoids isolated in the gel are incubated in the presence of cell extracts that are active for the first lesion incision step. The slides are then subjected to electrophoresis in an alkali medium. The presence of cleavage induces more rapid migration of the DNA than the nucleoid as a whole. The ball of DNA then has the appearance of a comet, the intact DNA being in the head and the DNA containing cleavages being in the tail of the comet. The percentage of DNA in the tail of the comet, determined by means of specialized software, correlates directly with the incision activity contained in the extracts used for the lesions under consideration. This assay has been applied to measuring activities of excision of oxidative damage in extracts originating from human lymphocytes. Compared with the method described by Redaelli et al., 1998, which measures the cleavage of plasmids, the method of Collins et al. uses the comet method to estimate strand cleavages and considers that this variant is, firstly, significantly more sensitive (detection of approximately 0.2 to 2 cleavages per $10^9$ daltons) and, secondly, economically advantageous (savings in terms of the material used), since the volume of reaction mixture (DNA included in a gel) is only 50 µl and a sufficient amount of material to be assayed is obtained from 10 ml of blood (possibility of carrying out several incubations).

D. International application WO 01/90408 describes a method for detecting and characterizing activities of proteins involved in DNA lesion repair.

More precisely, this method comprises the attachment to a solid support of at least one damaged DNA containing at least one known lesion; this damaged DNA is then subjected to the action of a repair composition containing or not containing at least one protein involved in the repair of this damaged DNA, and the determination of the activity of this protein for the repair by measuring the variation of a signal emitted by a label that attaches to or removes itself from the support during the preceding step.

This system, which is used with a damaged DNA that is in the form of an oligonucleotide of 15 to 100 bases or of a polynucleotide of 100 to 20 000 bases, thus makes it possible to obtain a more overall piece of information than the other assays, since the excision of several substrates can be monitored simultaneously.

However, this method concerns the demonstration of DNA lesion incision activities. It is thus limited to characterizing the step of excision of lesions that may be introduced into synthetic oligonucleotides. Furthermore, although it provides considerable information regarding excision activities, it is not suitable for and does not describe a precise quantification of the enzyme activities for excision/resynthesis of DNA.

Besides the drawbacks specific to each technique, reported above, these various methods also have the following drawbacks:

All the assays described above require the use of amounts of biological material and in particular of cell extracts of greater than 10 µl: the reaction volume generally used is 50 µl containing from 10 to 40 µl of extract for an amount of proteins of approximately 100 µg. The extracts take a long time to prepare, and the amount of available cells is often small, which limits the number of assays that can be carried out.

Whatever the detection method used and whether the assay is carried out in solution or on a support, all these systems described provide information regarding point-by-point repair limited to a given substrate for an aliquot fraction of extract; this is because, in the assays for determining repair capacities as proposed by Wood et al., for example, each assay is carried out individually in a tube, i.e. a reaction takes place in the presence of a given plasmid and of a given extract. For each extract to be tested, the rate of incorporation of the label into the plasmid is compared with the rate of incorporation of the label obtained in a substrate prepared in an identical manner in the presence of the control extract. The reference control extract is generally prepared from characterized cells transformed with EBV or SV40. The same is true in most of the other variants of the method by Wood et al., described above.

Since the assays are relatively laborious to carry out and require the availability of large amounts of biological material, experimenters limit the number of substrates used and the number of biological extracts tested.

The lesions introduced into the plasmids are neither measured nor quantified. The authors, using the assay developed by Wood et al., eliminate only the plasmids that have lost their supercoiled form, in order to eliminate DNA containing chain breakages. The information obtained is very partial and insufficient to precisely define and characterize the repair capacities of a given biological medium.

SUMMARY OF THE INVENTION

Consequently, the applicant gave itself the aim of overcoming the drawbacks of the prior art, in particular by proposing a method which makes it possible to characterize and to quantify the enzyme activities for excision/resynthesis for DNA repair in biological extracts in a rapid, precise, miniaturized and effective manner, without the use of control repair solutions.

A subject of the present invention is a method for the quantitative assessment of the overall and specific DNA repair capacities of at least one biological medium, which method is characterized in that it comprises the following steps:
(a) preparing a range of plasmids, each comprising distinct DNA lesions, by independent treatment of said various plasmids with at least one physical and/or chemical agent and recovery of the supercoiled fraction of each of said plasmids; selection of the supercoiled fractions makes it possible to exclude strand breakages and to avoid the action of nucleases,
(b) characterizing the lesions present on each of the plasmids of said range of plasmids,
(c) depositing the various plasmids of said range of plasmids, and at least one supercoiled control plasmid without lesions, onto a single solid support, according to a pre-established configuration A, so as to form a functionalized support divided into different zones $A_1$ to $A_x$, x corresponding to an integer equal to the number of biological media to be tested simultaneously, each zone $A_1$ to $A_x$ comprising said range of plasmids; consequently, the various preparations of plasmids of said range of modified plasmids are deposited onto the same solid support at defined and pinpointed sites. At least one control consisting of a supercoiled plasmid without DNA lesions is jointly deposited,
(d) incubating said functionalized support obtained in step (c) with various repair solutions, each comprising at least one biological medium that may contain enzyme activities for repair, ATP, an ATP-regenerating system, a labeled nucleotide triphosphate and any other component necessary for the activity of the repair enzymes present in said biological medium, preferably at a temperature of 30° C. for 1 to 5 hours, preferably for 3 hours, each of said repair solutions being deposited, prior to said incubation, in each of said different and pre-established zones $A_1$ to $A_x$ of said functionalized support,
(e) washing said functionalized support at least once,
(f) directly or indirectly measuring the signal produced by the label incorporated into the DNA during the repair reaction in step (d), in each of said different and pre-established zones $A_1$ to $A_x$,
(g) recording and quantifying the signal corresponding to each deposit of plasmid in each zone $A_1$ to $A_x$, and
(h) determining the ratio of the signals of the plasmids comprising the lesions relative to the control plasmid directly deposited.

DETAILED DESCRIPTION OF THE PREFERRED EMBODIMENTS

Figure 1:
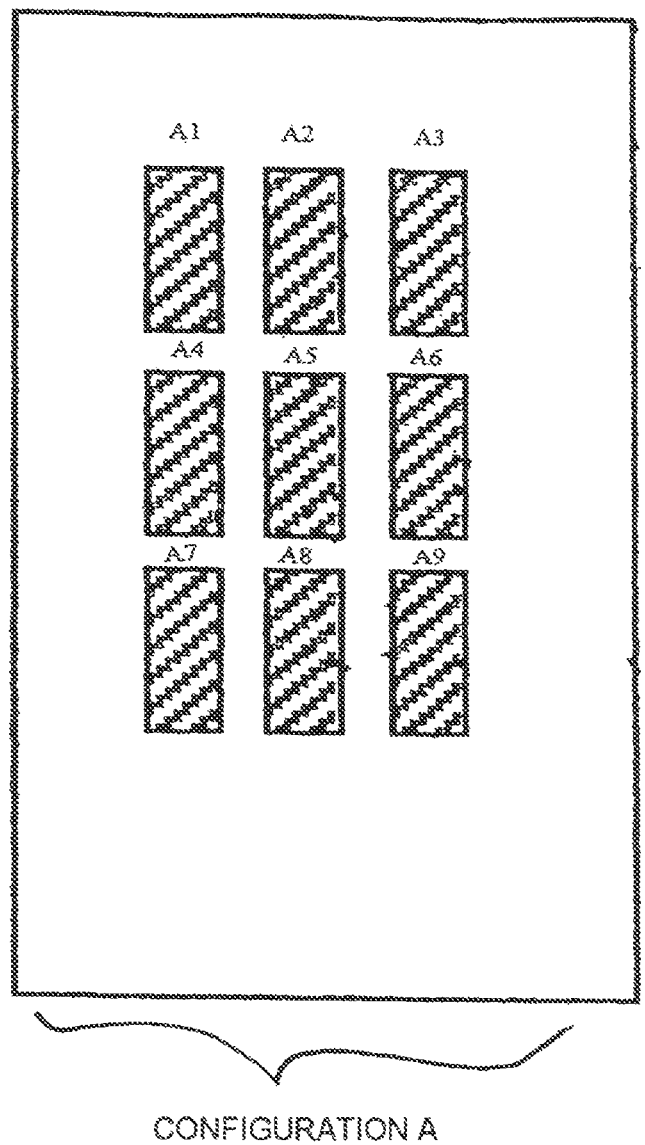
FIG. 1 illustrates an example of a solid support configuration; a plan of deposition in nine zones is observed.

Such a method according to the invention has a certain number of advantages:
  It makes it possible to detect an overall effect, while identifying the various lesions, due to the possibility of simultaneously assessing the repair of various types of lesions.
  It makes it possible to determine the excision and/or excision/resynthesis capacities of a biological extract without resorting to comparison with a control biological medium. This is because the results obtained by carrying out the method with a single sample of biological extracts are sufficient to accord the extract a repair effectiveness with respect to precise and quantified lesions.
  It is particularly suitable for studying various biological media and is a good reflection of the situation in vivo.
  The method according to the invention makes it possible to "map" a given biological medium in terms of its enzyme activities for DNA repair. It makes it possible to identify a biological extract according to the map obtained.
  It makes it possible to determine the repair proteins that are deficient or partially deficient in a given biological extract and therefore to serve as a diagnostic test.
  The method according to the invention also makes it possible to compare the performance levels of various biological extracts in terms of DNA lesion repair.
  It does not use any radioactive isotope.
  Since it is miniaturized, it makes it possible to obtain numerous pieces of information using very small amounts of biological material.
  It can be automated.

According to an advantageous embodiment of said method, the plasmids prepared in step (a) are chosen from those that have a double-stranded supercoiled form (pBR322, M13, pUC, etc).

The supercoiled form of the control plasmid is obtained by purification using known techniques, for instance the Qiagen plasmid purification kits. It is also preferable to limit the presence of unwanted plasmid forms by carrying out other purification steps, for instance cesium chloride centrifugation and/or sucrose gradient centrifugation.

According to another advantageous embodiment of step (a) of said method, the various physical, biological or chemical agents capable of inducing a lesion of the DNA are chosen from those that preferably induce: the formation of a single lesion, the formation of a limited number of lesions or the formation of various lesions belonging to the same family.

As families of lesions, mention may, for example, be made of: oxidative lesions, photoproducts induced by ultraviolet B or C radiation, chemical adducts, etheno-bases, abasic sites and DNA breakages.

The physical and chemical agents are, for example, chosen from those that function mainly:

via a type II photosensitization mechanism: the main target of singlet oxygen is guanine; in this case, the abundant lesion formed is 8-oxoguanine (Ravanat et al., Chem. Res. Tox., 1995, 8, 379-388);

via a type I photosensitization mechanism or via a mechanism that releases the OH° radical; in this case, the DNA lesions obtained are oxidative lesions; these lesions affect the purine bases and the pyrimidine bases in the DNA in an equivalent manner. Among these lesions, mention may be made of 8-oxoguanine, glycols, thymine, fapy-guanine, fapy-adenine, hydroxymethyl-uracil, 5-hydroxymethylcytosine and formyluracil (Cadet et al., Rev. Physiol. Biochem. Pharm., 1997, 31, 1, 87);

via a mechanism of triplet-triplet energy transfer; in this case, the main lesions formed are cyclobutane pyrimidine dimers (Costalat et al., Photochem, Photobiol., 1990, 51, 255-262);

by releasing energy absorbed directly by the DNA bases, such as ultraviolet B or c radiation. The linkages formed are cyclobutane pyrimidine dimers, (6-4) photoproducts and the Dewar valence isomer (Douki et al., J. Biol. Chem., 2000, 275, 11678-11685);

by releasing singlet oxygen. These agents belong, for example, to the endoperoxide family. The lesion formed is, in this case, 8-oxoguanine (Ravanat et al., J. Biol. Chem., 2001, 276, 40601-40604).

The chemical agents are chosen from those that induce known base modifications, belonging, inter alia, to the carcinogen family. Mention may, for example, be made of: acetylaminofluorene (Hess et al., 1996, Nucleic Acid Res. 24, 824-828), cisplatin (Pasheva et al., 2002, Int. J. Biochem. Cell. Biol., 34, 87-92), benzopyrene (Laws et al., 2001, Mut. Res.; 484, 3-18), psoralen (Zhang et al., Mol. Cell. Biol., 2002, 22, 2388-2397), chloroacetaldehyde (CAA—Wang et al., 2002, 13, 1149-1157), tamoxifen (Dasaradhi et al., 1997, Chem. Res. Tox., 10, 189-196) and trans, trans-2,4-decadienal (DDE—Carvalho et al., 1998, Chem. Res. Tox., 11, 1042-1047).

According to yet another advantageous embodiment of step (a) of said method, various agents are used on each plasmid of said range of plasmids.

According to an advantageous embodiment of step (b) of said method, the characterization of the lesions comprises (i) taking a fraction of each plasmid with lesions, (ii) digesting each of said fractions with enzymes that release the nucleosides from the DNA, and then (iii) analyzing the result of the digestion using a combination of separative techniques coupled to a quantitative analytical technique.

According to an advantageous arrangement of this embodiment, the digestion is carried out using at least one of the following enzymes: calf spleen phosphodiesterase, P1 nuclease, snake venom phosphodiesterase, and alkaline phosphatase (Douki et al., J. Biol. Chem., 2000, 275, 11678-11685).

According to another advantageous arrangement of this embodiment, the result of the enzyme digestion is analyzed by means of one of the following techniques: high performance liquid chromatography (HPLC) coupled to tandem mass spectrometry (Douki et al., 2000, J. Biol. Chem., 275, 11678-11685; Sauvaigo et al., 2001, Photochem. Photobiol., 73, 230-237; Frelon et al., Chem. Res. Tox., 2000, 13, 1002-1010), by HPLC coupled to gas chromatography (Wang et al., 2000, 13, 1149-1157; Pouget et al., 2000, Chem. Res. Tox., 13, 541-549) or else by HPLC coupled to electrochemical detection (Pouget et al., 2000, Chem. Res. Tox., 13, 541-549).

According to another advantageous embodiment of said method, prior to step (c), the supercoiled forms of the plasmid obtained in step (a) are purified, preferably by sucrose gradient centrifugation and/or cesium chloride gradient centrifugation.

According to another advantageous embodiment of said method, also prior to step (c), each of the plasmids of the range of plasmids is diluted to a concentration of between 5 and 100 µg/ml, in a diluting buffer preferably comprising a buffer at a pH of between 6.5 and 8.0, optionally combined with a salt and with a nonionic surfactant; preferably, said buffer is a 10 mM phosphate buffer or an SSC buffer, that can contain 0.05M to 0.5M NaCl.

The various plasmids are preferably deposited using a robot intended for the production of microarrays, i.e., the volumes deposited are preferably between 100 and 1000 picoliters.

According to an advantageous embodiment of step (c) of said method, said support is a support that has been sensitized so as to increase its affinity for the DNA, selected from the group consisting of organic or inorganic materials chosen from glass, silicon and its derivatives, and synthetic or nonsynthetic polymers (nylon or nitrocellulose membranes), and the surface of which is optionally functionalized; preferably, said support consists of glass slides coated with poly-L-lysine that adsorb the DNA, or glass slides functionalized with epoxy groups that form covalent bonds with the DNA.

If necessary, treatments are performed so as to increase the attachment of the DNA to its support. These treatments must not create additional lesions in the deposited DNA.

A standard support according to the invention comprising zones $A_1$ to $A_x$, each zone comprising the entire range of plasmids, comprises, in each of said zones:
at least one deposit of control plasmid, and
a deposit of plasmid containing photoproducts, and/or
a deposit of plasmid containing oxidative damage, and/or
a deposit of plasmid containing etheno-bases, and/or
a deposit of plasmid containing DNA breakages, and/or
a deposit of plasmid containing carcinogenic agent adducts.

In accordance with step (d) of the method according to the invention:
the biological extract can be prepared from the biological medium, according to the method of Manley et al., 1983, Methods Enzymol. 101, 563-582 or according to the method of Biade et al., J. Biol. Chem., 1998, 273, 898-902, or according to any other method capable of providing a medium containing repair proteins;
the label is selected from affinity molecules, fluorescent compounds, antibodies or biotin; preferably, the label or agent for visualizing the label is in particular chosen from the group consisting of fluorescent compounds with direct fluorescence (Cy-3 or Cy-5) or indirect fluorescence (biotin or digoxigenin);
the support is then incubated at a temperature that promotes the repair reaction, preferably 30° C., for a period of between one and five hours, preferably for three hours.

According to an advantageous embodiment of step (e) of the method according to the invention, the support is washed at least once with a saline solution containing a nonionic surfactant, in particular a 10 mM phosphate buffer, containing Tween 20, and is then subsequently rinsed with water at least once.

In accordance with step (f) of the method according to the invention, the signal is measured by means of a method suitable for the label; for example, if the label is a fluorophore, direct measurement of the fluorescent signals emitted by the various deposits on the support is carried out.

According to an advantageous embodiment of step (g) of the method according to the invention, said signals are quantified using a device capable of exciting the label, preferably a fluorophore, and of measuring the signal emitted subsequent to the excitation.

The signal is measured by means of instrumentation suitable for the support and for the label used. A scanner may be used for the fluorescence image analysis, preferably with laser excitations at the wavelength specific for the label used.

According to an advantageous embodiment of step (h) of the method according to the invention, a numerical ratio of the signals obtained with the plasmids containing the lesions to the signal obtained with the control plasmid located on the same support is established.

According to the invention, a repair profile of a given biological medium is thus obtained.

This repair profile can be used to determine the overall and specific repair capacities of a medium, to diagnose a repair-related disease, or to assess the influence of a physical or chemical treatment (genotoxic product, for example) on the repair capacities of a given medium.

Consequently, a subject of the present invention is the use of the method as defined above:
- for establishing the repair profile of a biological medium,
- for diagnosing a repair-related disease,
- for assessing the influence of a physical or chemical treatment on the repair capacities of a given biological medium,
- for screening substances capable of modulating the repair system of a biological medium.

Figure 2:
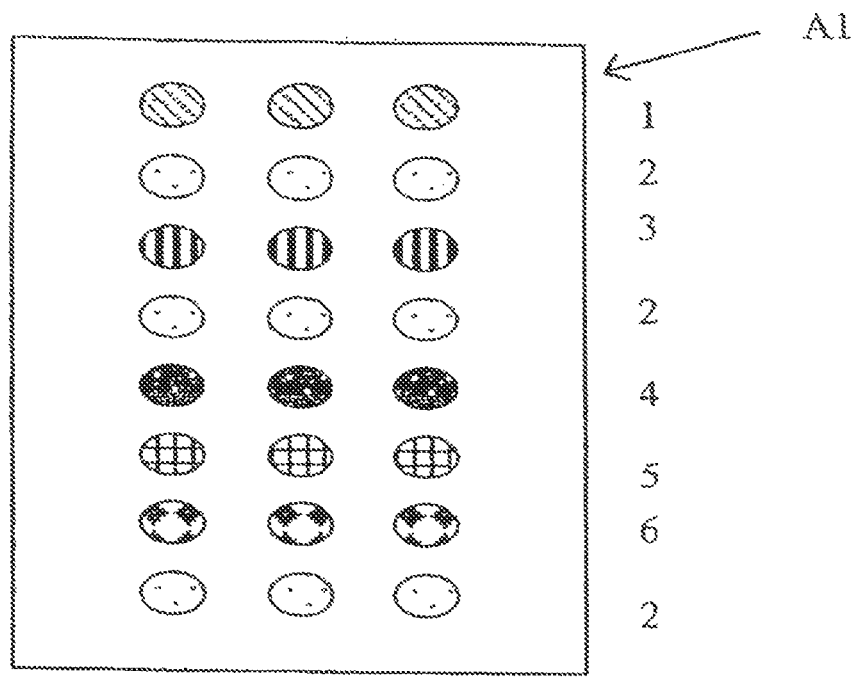
FIG. 2 represents a deposition plan of each zone.

Besides the above arrangements, the invention also comprises other arrangements, that will emerge from the following description, that refers to examples of implementation of the method that is the subject of the present invention and also to the attached drawings, in which:

FIG. 1 illustrates an example of configuration of the solid support; a plan of deposition in nine zones is observed;

FIG. 2 represents the deposition plan of each zone; and

Figure 3:
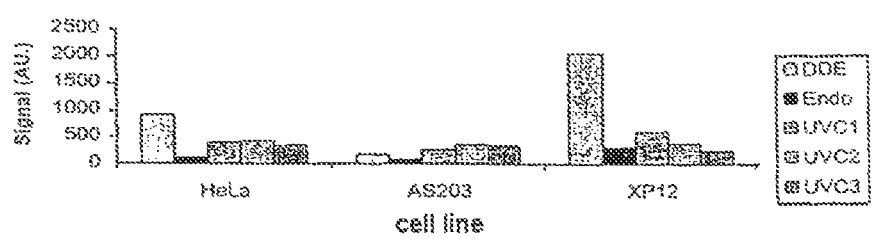
FIG. 3 represents a repair diagram-repair mapping associated with each cell line that was used to prepare the extract used for the repair reaction.

FIG. 3 represents a repair diagram—repair mapping associated with each cell line that was used to prepare the extract used for the repair reaction.

It should be clearly understood, however, that these examples are given only by way of illustration of the subject of the invention, of which they in no way constitute a limitation.

Example 1

Preparation of the Range of Plasmids and Assaying of the Lesions

The plasmid pBluescript II is produced by transformation of XLI-Blue MRF supercompetent cells from Stratagene, according to the protocol provided by Stratagene.

The plasmid is then purified using the Qiagen plasmid midi kit, according to the recommended protocol.

Additional Purification of the Plasmid

The plasmid is loaded onto 10 ml of 5-20% sucrose gradient in a 25 mM Tris HCl buffer, pH 7.5; 1M NaCl; 5 mM EDTA and centrifuged in a Beckman ultracentrifuge using an SW-41 rotor, at 4° C. and at 25 000 rpm for 18 hours. 1 ml fractions are then carefully taken and analyzed on an agarose gel. Only the fractions containing at least 90% of coiled form of the plasmid are kept. The plasmid is precipitated with ethanol and dissolved in PBS.

Plasmid Modifications

UVC Irradiation—Formation of Cyclobutane Pyrimidine Dimers (CPDs) and of (6-4) Photoproducts The plasmid, diluted to 20 g/ml in a PBS, is irradiated using a Bioblock germicidal lamp equipped with two 15-Watt neons. Three plasmid preparations are irradiated, respectively, at 0.06; 0.12 and 0.2 J/cm$^2$.

Treatment with Chloroacetaldehyde (CCA-Signa)—Formation of Malondialdehyde-Deoxyguanine (MDA-dG)

The plasmid is prepared at 1 mg/ml in PBS, and an equivalent volume of CAA (50% in $H_2O$) is added. This solution is incubated overnight at 37° C. The plasmid is recovered by precipitation and purified on a sucrose gradient.

Treatment with trans,trans-2-4-decadienal (DDE-Sigma)—Formation of Etheno-Guanosine and of Etheno-Adenosine 200 µl of 0.2M carbonate/bicarbonate buffer, pH 9.2 and an equivalent volume of THF are added to 200 µl of plasmid prepared in water at 1 mg/ml. 4 µl of DDE and 12 µl of 30% $H_2O_2$ are then added. The solution is incubated for 2 hours at 50° C. in the dark. The DDE is eliminated by means of two extractions with dichloromethane. The DNA is precipitated and then purified on a sucrose gradient.

Treatment with Endoperoxide $DHPNO_2$—Formation of 8-oxo-2'-deoxiguanosine (8-Oxo-dG)

20 µl of the solution of endoperoxide (N,N'-di(2,3-dihydroxypropyl)-1,4-naphthalenedipropanamide 1,4-endoperoxide), prepared according to the protocol described in J. Biol. Chem., 2000, 275, 40601-40604, are incubated in 200 µl of plasmid diluted to 1 mg/ml in PBS, for 2 hours at 37° C. The plasmid is then precipitated and purified on a sucrose gradient.

Assaying of the Lesions in the Plasmids

A fraction of plasmid DNA or of calf thymus DNA treated under the same conditions is taken for analysis of the modified base composition.

The DNA is digested as described by Douki et al., J. Biol. Chem., 275, 11678-11685, and the analysis is then carried out by HPLC-tandem mass spectrometry.

The following amount of lesions per $10^4$ normal bases is obtained:

| Treatment | Etheno Da | Etheno Dg | MDA-Dg | 8-oxo-Dg | Pyrimidine dimer | (6-4) photo-product |
|---|---|---|---|---|---|---|
| Control DNA | 0.11 | 0.00 | 0.00 | 0.61 | | |
| Endoperoxide | 0.01 | 0.00 | 0.02 | 6.15 | | |
| DDE | 1.42 | 9.04 | 0.24 | 2.89 | | |
| UVC 0.06 J/cm$^2$ | | | | 0.12 | 5.03 | 0.45 |
| UVC 0.12 | | | | 0.18 | 11.08 | 0.93 |
| UVC 0.2 J/cm$^2$ | | | | 0.21 | 18.14 | 1.57 |

It is noted that the treatments bring about the formation of lesions in very different proportions:
- the UVC radiations bring about, to a very large extent, the formation of cyclobutane pyrimidine dimers (CPDs) and, to a minor extent, the formation of (6-4) photoproducts, the DDE brings about the predominant formation of etheno-deoxyguanosine, the endoperoxide brings about the very predominant formation of 8-oxo-2'-deoxyguanosine.

It is seen that these agents make it possible to induce the predominant formation of specific lesions targeting precise families of repair enzymes.

Example 2

Implementation of the Method According to the Invention with the Range of Plasmids Prepared in Example 1

Deposition of the Plasmids onto a Support

The plasmids are diluted to 20 µg/ml in PBS. 500-picoliter deposits are made, using a GESIM robot, on commercial poly-L-lysine-coated glass slides (VWR). The slides are conserved at 4° C.

Each slide (support S) comprises 9 identical zones (A1 to A9) arranged according to configuration A in FIG. 1.

In each zone, the range of plasmids is deposited in accordance with FIG. 2, which illustrates, for example, zone A1.

Each zone makes it possible to test a different biological medium.

Repair Reaction

A solution is prepared containing the biological medium or extract to be tested; for 5 µl of solution, the composition is as follows:

| | |
|---|---|
| extract | 0.5 µl |
| 5x repair buffer | 1 µl |
| CY5-dUTP (Amersham Pharmacia Biotech) (0.1 nmol/µl) | 0.2 µl |
| 2M KCl | 0.2 µl |
| ATP (Roche - 100 mM) | 0.1 µl |

The volume is made up to 5 µl with $H_2O_2$.

Composition of the 5× Repair Buffer:

Hepes/KOH, 200 mM, pH 7.8; 35 mM $MgCl_2$; 2.5 mM DTT; 2 µM dATP, 2 µM dGTP; 2 µM dCTP; 50 mM phosphocreatine; 250 µg/ml creatine phosphokinase; 0.5 mg/ml BSA; 17% glycerol.

Cell Lines Used

The example is performed with three different extracts originating from different cell lines:

Line 1: these are HeLa cells. The extracts are commercial nuclear extracts and come from the company 4C Biotech (Belgium). They were prepared by the method of Dignam et al., (Nucl. Ac. Res., 1983, 11, 1475-1489). Their protein content is 24 mg/ml.

Line 2: this is a line of AS203 cells established from a patient suffering from *xeroderma pigmentosum*, complementation group D. The extracts were prepared according to the protocol of Manley et al. Assaying of proteins using the micro BCA kit makes it possible to evaluate the amount of proteins at 44 mg/ml.

Line 3: these are XP12RO cells. This line was established from a patent suffering from *xeroderma pigmentosum*, complementation group A. The extracts were prepared according to the protocol of Manley et al., (Methods Enzymol., 1983, 101, 568-582). The extract obtained contains 36 mg/ml of proteins (micro BCA assay kit, Interchim).

3 µl of each repair solution are deposited onto all the deposits of a single zone of the slide. The slide is incubated at 30° C., under moist conditions, for 3 hours. The slide is washed 3 times for 10 minutes in a PBS buffer containing 0.1% of Tween 20. It is then washed in $H_2O$ for 15 minutes. After drying, the fluorescence is read.

Analysis of Repair Signals

After the repair reaction, the fluorescence of the various deposits of each zone is analyzed by means of an Axon scanner at 635 nm and the GenePix Pro analytical software. A mean of three identical points is then determined. A value is thus obtained for each type of modification. A diagram is plotted for each cell line. This diagram corresponds to a mapping of the repair systems associated with the lesions present on the support or chip, and is specific for the extract used. The results obtained are given in FIG. 3. The level of fluorescence is given in arbitrary units (AU).

It is observed that each diagram is unique and specific for the cell line that was used to prepare the cell extract used. It can therefore be used to precisely characterize the overall repair activities of a given cell extract, and reveals the functionality of the systems targeted.

It is observed that the HeLa line repairs lesions induced by DDE (predominantly etheno-dG) twice as effectively as it does lesions induced by UV radiation (predominantly CPD and (6-4)). It is observed that the oxidative damage (predominantly 8-oxo-dG) is repaired much more weakly.

For the AS203 line, the highest level of repair, although it is low, is observed for the UV-induced lesions.

As regards the XP12RO line, it is observed that the DDE-induced lesions (predominantly etheno-dG) are the most effectively repaired, giving a signal three times higher than in the case of UVC radiation. It is known that the XPA lines do not repair CPDs; the signals obtained with UVC-irradiated DNA can thus be attributed to the repair of (6-4) photoproducts.

An unexpected advantage of the invention is that, even if the amount of protein is different from one extract to the other, the ratio obtained for the signals of the DNAs comprising the lesions to the signal of the control DNA, for a given extract, can be used to compare the repair capacities of the various extracts with respect to one another.

What is claimed is:

1. A method for quantitative assessment of the base excision repair (BER) and nucleotide excision repair (NER) DNA repair capacities of at least one cellular extract, which method comprises the following steps of:
   a) preparing a range of plasmids, each comprising distinct DNA lesions, by independent treatment of said plasmids with at least one physical or chemical treatment or both and recovering a supercoiled fraction of each of said plasmids,
   b) characterizing the lesions present on each of the plasmids of said range of plasmids,
   c) depositing the plasmids of said range of plasmids, and at least one supercoiled control plasmid without lesions, onto a single solid support, according to a pre-established configuration A, so as to form a functionalized support divided into different zones $A_1$ to $A_x$, x corresponding to an integer equal to the number of cellular extracts to be simultaneously tested, each zone $A_1$ to $A_x$ comprising, the following deposits of plasmids:
      at least one deposit of control plasmid,
      a deposit of plasmid containing photoproducts,
      a deposit of plasmid containing oxidative damage, and
      a deposit of plasmid containing etheno-bases, d) incubating said functionalized support obtained in step (c) with various repair solutions, each of which comprises at least one cellular extract from a subject, labeled nucleotide triphosphates, and a single repair buffer;

e) washing said functionalized support at least once, f) directly or indirectly measuring the signal produced by said labeled nucleotide triphosphate incorporated into the DNA during the repair reaction in step (d), in each of said different and pre-established zones $A_1$ to $A_x$, g) recording and quantifying the signal corresponding to each deposit of plasmid in each zone $A_1$ to $A_x$, and h) determining the ratio of the signals of the plasmids comprising the lesions relative to the control plasmid jointly deposited.

2. The method of claim 1, wherein the plasmids according to step (a) have a double-stranded supercoiled form.

3. The method of claim 1, wherein, in step (a) multiple treatment means are used on each plasmid of said range of plasmids.

4. The method of claim 1, wherein, in step (b) the characterizing of the lesions comprises (i) taking a fraction of each plasmid with lesions, (ii) digesting each of said fractions with enzymes that release the nucleosides from the DNA, and then (iii) analyzing the result of the digestion using a combination of separative techniques coupled to a quantitative analytical technique.

5. The method of claim 1, wherein the digestion is carried out using at least one of the following enzymes: calf spleen phosphodiesterase, P1 nuclease, snake venom phosphodiesterase, or alkaline phosphatase.

6. The method of claim 4, wherein the result of the enzyme digestion is analyzed by means of one of the following techniques: high performance liquid chromatography (HPLC) coupled to tandem mass spectrometry, by HPLC coupled to gas chromatography or by HPLC coupled to electrochemical detection.

7. The method of claim 1, wherein prior to step (c), the supercoiled forms of the plasmids obtained in step (a) are purified by sucrose gradient centrifugation or cesium chloride gradient centrifugation or both.

8. The method of claim 1, wherein, also prior to step (c), each of the plasmids of the range of plasmids is diluted to a concentration of between 5 and 100 µg/ml, in a diluting buffer.

9. The method of claim 8, wherein said buffer has a pH of between 6.5 and 8.0.

10. The method of claim 8, wherein said buffer further optionally comprises a salt and a non-ionic surfactant.

11. The method of claim 1, wherein, in step (c) the volumes of the deposits of the range of plasmids are between about 100 and 1000 picoliters.

12. The method of claim 1, wherein, in step (c), said support is a support that has been sensitized so as to increase its affinity for the DNA, and is an organic or inorganic material selected from the group consisting of glass, silicon and compounds thereof, and synthetic or non-synthetic polymers, and the surface of which is optionally functionalized.

13. The method of claim 12, wherein said support consists of glass slides coated with poly-L-lysine that adsorb the DNA, or glass slides functionalized with epoxy groups that form covalent bonds with the DNA.

14. The method of claim 12, wherein said support comprises different zones $A_1$ to $A_x$, each of said zones comprising the following deposits of plasmids:

a) at least one deposit of control plasmid, b) a deposit of plasmid containing photoproducts, c) a deposit of plasmid containing oxidative damage, d) a deposit of plasmid containing etheno-bases, e) a deposit of plasmid containing DNA breakages, and f) a deposit of plasmid containing carcinogenic substance adducts.

15. The method of claim 1, wherein in step e), the support is washed at least once with a saline solution containing a nonionic surfactant, comprising a 10 mM phosphate buffer containing Polysorbate 20, and is then subsequently rinsed with water at least once.

16. The method of claim 1, wherein in step f), the signal is measured by means of a method suitable for the labeled nucleotide triphosphate.

17. The method of claim 1, wherein, in step (g), said signals are quantified using a device capable of exciting label of the labeled nucleotide triphosphate, and of measuring the signal emitted subsequent to the excitation.

18. The method of claim 17, wherein, in step (h) of the method, a numerical ratio of the signals obtained with the plasmids containing the lesions to the signal obtained with the control plasmid located on the same support is established.

19. The method of claim 1, wherein the quantitative assessment is for establishing a repair profile of the at least one cellular extract.

20. The method of claim 1, wherein the quantitative assessment is for diagnosing a base excision repair (BER) or nucleotide excision repair (NER) DNA repair-deficiency disease.

21. The method of claim 1, wherein the quantitative assessment is for assessing the influence of a physical or chemical treatment on repair capacities of the at least one cellular extract.

22. The method of claim 20, wherein said base excision repair (BER) or nucleotide excision repair (NER) DNA repair-deficiency disease is selected from the group consisting of Xeroderma pigmentosum, Cockayne Syndrome, Ataxia Telangectasia and cancer.

23. The method of claim 20, wherein said base excision repair (BER) or nucleotide excision repair (NER) DNA repair-deficiency disease is Xeroderma pigmentosum.

24. The method of claim 1, wherein the quantitative assessment is for screening substances capable of modulating a repair system of the at least one cellular extract.

25. The method of claim 1, wherein in step d), said incubating is effected at a temperature of about 30° C. for 1 to 5 hours.

26. The method of claim 25, wherein said incubating is for 3 hours.

27. The method of claim 1, wherein said distinct DNA lesions of step a) comprise oxidative lesions, photoproducts induced by ultraviolet B or C radiation, chemical adducts, etheno-bases, abasic sites and DNA breakages.

28. The method of claim 1, wherein the depositing of plasmids in step c) is conducted by a robot for producing microarrays.

29. The method of claim 1, wherein the labeled nucleotide triphosphate is labeled with $^{32}P$.

30. The method of claim 1, wherein the repair solutions of step d) comprise enzyme activities for repair, and any other components necessary for the enzyme activities.

* * * * *